US00PP36629P2

(12) United States Plant Patent
Whitbeck

(10) Patent No.: US PP36,629 P2
(45) Date of Patent: Apr. 22, 2025

(54) ZOYSIAGRASS NAMED 'Frank Whitbeck Hime Korai'

(50) Latin Name: *Zoysia matrella*
Varietal Denomination: Frank Whitbeck Hime Korai

(71) Applicant: Winrock Grass Farm, Inc., Little Rock, AR (US)

(72) Inventor: Frank Butterfield Whitbeck, Little Rock, AR (US)

(73) Assignee: Winrock Grass Farms, Inc., Little Rock, AR (US)

( * ) Notice: Subject to any disclaimer, the term of this patent is extended or adjusted under 35 U.S.C. 154(b) by 0 days.

(21) Appl. No.: 18/584,137

(22) Filed: Feb. 22, 2024

(51) Int. Cl.
*A01H 5/12* (2018.01)
*A01H 6/46* (2018.01)

(52) U.S. Cl.
USPC ..... Plt./390

(58) Field of Classification Search
USPC ..... Plt./390
See application file for complete search history.

(56) References Cited

U.S. PATENT DOCUMENTS

PP29,201 P2 * 4/2018 Engelke ..... A01H 6/469 Plt./390

OTHER PUBLICATIONS

"International Code of Nomenclature for Culitvated Plants," Ninth Edition, Published by ISHS Jun. 2016, (15 pages total).*

* cited by examiner

*Primary Examiner* — Susan McCormick Ewoldt

(57) ABSTRACT

A new and distinct variety of *matrella* Zoysiagrass named "Frank Whitbeck Hime Korai" is characterized by an ultra-dwarf leaf canopy with exceptional density at lower golf green mowing heights, extremely high tolerance to summer heat and winter cold, even at lower golf green mowing heights, exceptional four-season green color retention, an exceptional year-round plant health in both full sunshine and shade, even in lower golf green mowing heights, exceptional natural resistance to cool season and warm season weeds, including contamination from other grasses, exceptional natural resistance to plant diseases and pests, exceptionally low need for fertilization, especially nitrogen, at all mowing heights, and exceptionally fast recovery from divot injury, sod harvesting and foot traffic wear.

12 Drawing Sheets

Genus and species: The genus and species of the novel variety described herein is *Zoysia matrella.*

Variety denomination: The novel variety described herein has been given the variety denomination "Frank Whitbeck Hime Korai.".

BACKGROUND OF THE INVENTION

In the fall of 1997 the inventor personally selected the original specimen of the *Zoysia matrella* variety claimed herein from a cultivated area at a golf course nursery located near Jinsekikogen in Prefecture Hiroshima, Japan, as it piqued his interest due to certain unique properties not exhibited by other Zoysiagrass plants based on his knowledge of Zoysiagrass plants. The cultivated area where the original specimen was selected was not contaminated with other Zoysiagrass plants. The inventor immediately sent the new claimed variety specimen to the quarantine section of the United States Department of Agriculture (USDA) at Beltsville, Maryland, the variety at the time labeled "hime korai." Following one year of quarantine, the inventor received a small pot of the new claimed variety from the USDA quarantine section. The inventor then asexually reproduced the new claimed variety on the irrigated pure fertile ground at his farm near Little Rock, Arkansas by removing bareroot stolons and rhizomes of the new claimed variety from the pot and planting them just under the soil surface on six-inch centers. The initial grow-in from planted sprigs of the new claimed variety to fully maturity establishment took almost two full growing seasons. Noxious cool season and warm season weeds were removed chemically during the grow-in process. Subsequently the inventor took bareroot stolons and rhizomes from the then-mature small plot of the new claimed variety and planted them just beneath the soil surface on a slightly larger plot of irrigated pure fertile ground at his farm near Little Rock, Arkansas. This second asexual grow-in also took approximately two full growing seasons to grow together to a full maturity establishment. This planting process was replicated every two years until the inventor had a one-acre nursery plot with which to study and observe the characteristics of the new claimed variety. No other Zoysiagrass plants, noxious weeds or other weed grasses were allowed to contaminate this new nursery stock area planted with the new claimed variety. Once there was enough plant material of the new claimed variety, plug planting on six-inch centers was adopted for a continuation of the asexual grow-in of a pure nursery stock of the new claimed variety on larger acreage at the inventor's farm near Little Rock, Arkansas. The parent plant of the new claimed variety is unknown.

UNIQUE CHARACTERISTICS OF THE NEW VARIETY

"Frank Whitbeck Hime Korai" is a new and distinct *Zoysia matrella* ultradwarf variety with novel characteristics that separate it from all other known *Zoysia matrella* varieties. Included in these unique characteristics are:

An exceptionally dense root system that fully develops and thrives in the United States transition zone and in warmer zones.

An ultradwarf leaf canopy with exceptional density, especially at lower golf green mowing heights.

A high tolerance to extreme summer heat and to sub-zero centigrade winter cold temperatures, even at lower golf green mowing heights.

An exceptional four-season green color retention in its ultradwarf leaf blade canopy, even in the face of lower winter cold temperatures and lower golf green mowing heights.

An exceptional year-round plant health in both full sunshine and lower light levels (i.e. shade), even in lower winter cold temperatures and lower golf green mowing heights.

An exceptional stability in a wide range of weather conditions as during its many years of outdoor testing and observation in sun, shade, cold and heat there was no change or visible mutation in the plant itself nor was there a need that required tarps for protection from winter cold conditions. The plant does go dormant, mainly during January and February when properly maintained, but only rarely goes 100% dormant in the United States transition zone.

An exceptional natural resistance to cool season and warm season weeds, including contamination from other grasses.

An exceptional natural resistance to plant diseases and pests, hence its need for herbicide, fungicide and pesticide treatments are minimal following establishment.

An exceptionally low need for fertilization, especially nitrogen, in order to thrive and retain green color at all mowing heights in all seasons.

An exceptionally fast recovery from divot injury, sod harvesting, and foot traffic wear for a warm season *Zoysia matrella* grass with high tolerance for winter cold temperatures.

United States Department of Agriculture plant hardiness zones 6-9 are all candidates for the claimed plant variety. Hence, some two-thirds of the United States will benefit from the positive low fertility and low herbicide use characteristics of the claimed plant variety, assuming adequate irrigation is in place.

BRIEF DESCRIPTION OF THE PHOTOGRAPHS

DESCRIPTION OF THE NEW VARIETY

Figure 1:
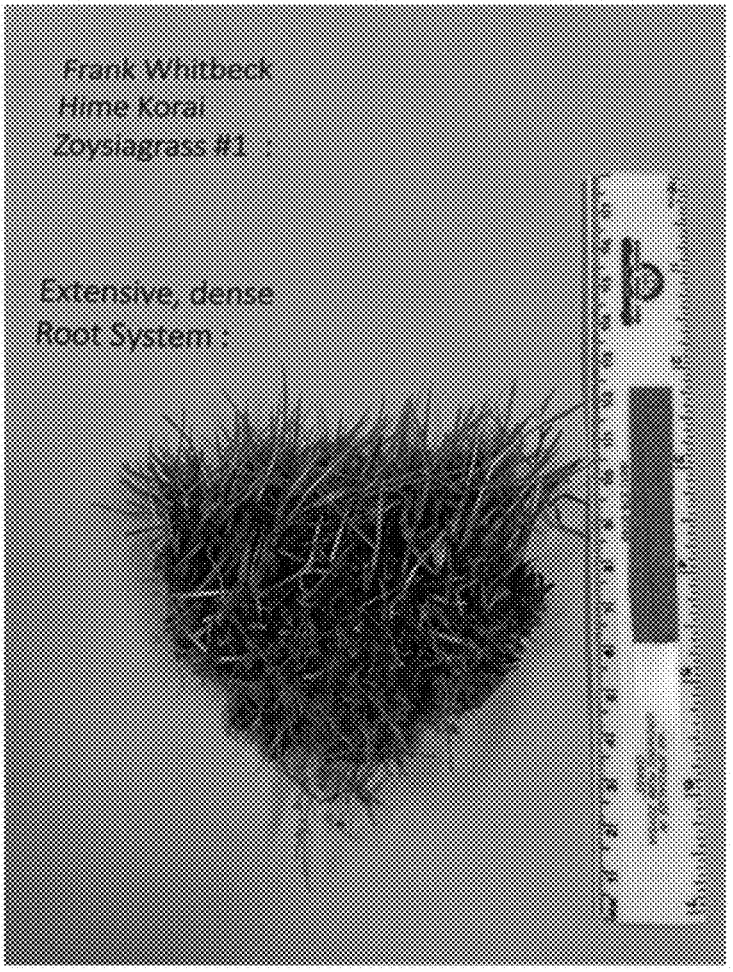
FIG. 1 is a photograph showing the root system of the claimed new variety.

Root System:

The new variety is identified by its extremely dense root mass of intertwined stolons and rhizomes about 1 millimeter in width, as shown in FIG. 1. Root stems may exceed 1 foot in length in all directions within the subsurface soil or along the surface of the soil base. As with its ultradwarf leaf canopy, the new variety's root mass at full establishment is so dense that it appears to crowd out any competing weed or competing grass from taking hold. This characteristic is so dominant that, in addition to its propensity to enjoy an extremely high level of natural plant health in all seasons, the plant needs very little help from amendments such as herbicides, fungicides and fertilizers. Use of these amendments at full establishment can be characterized as "occasional" rather than "seasonal" or even "annual" assuming regular mowing at a preferred mowing height with adequate irrigation during summer and fall.

Figure 2:
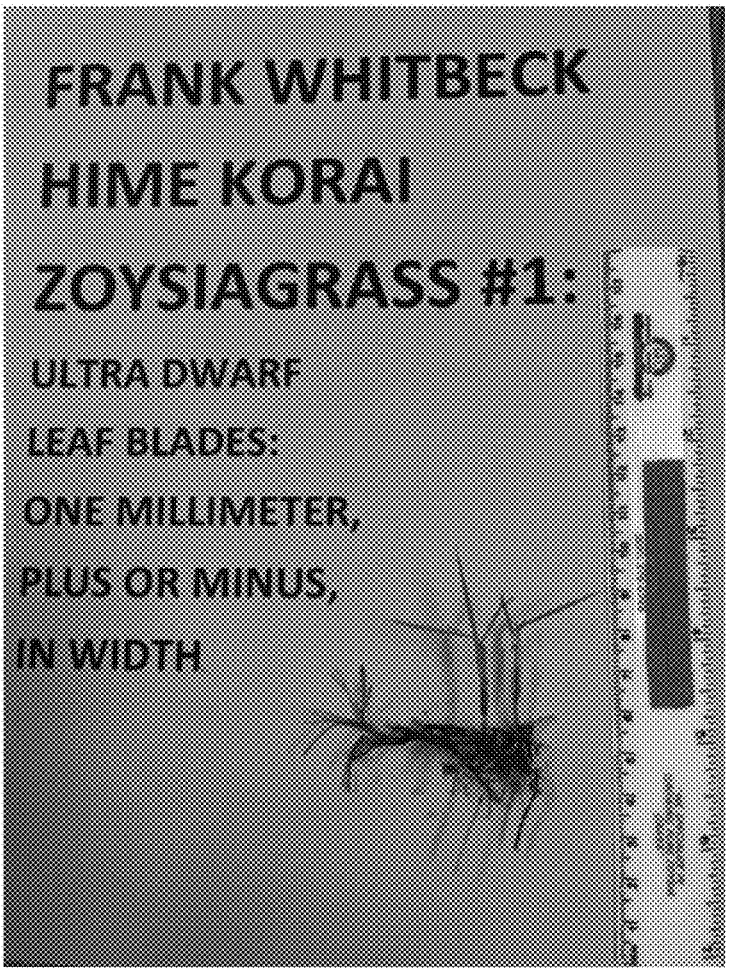
FIG. 2 is a first photograph showing leaves of the claimed new variety.
Figure 3:
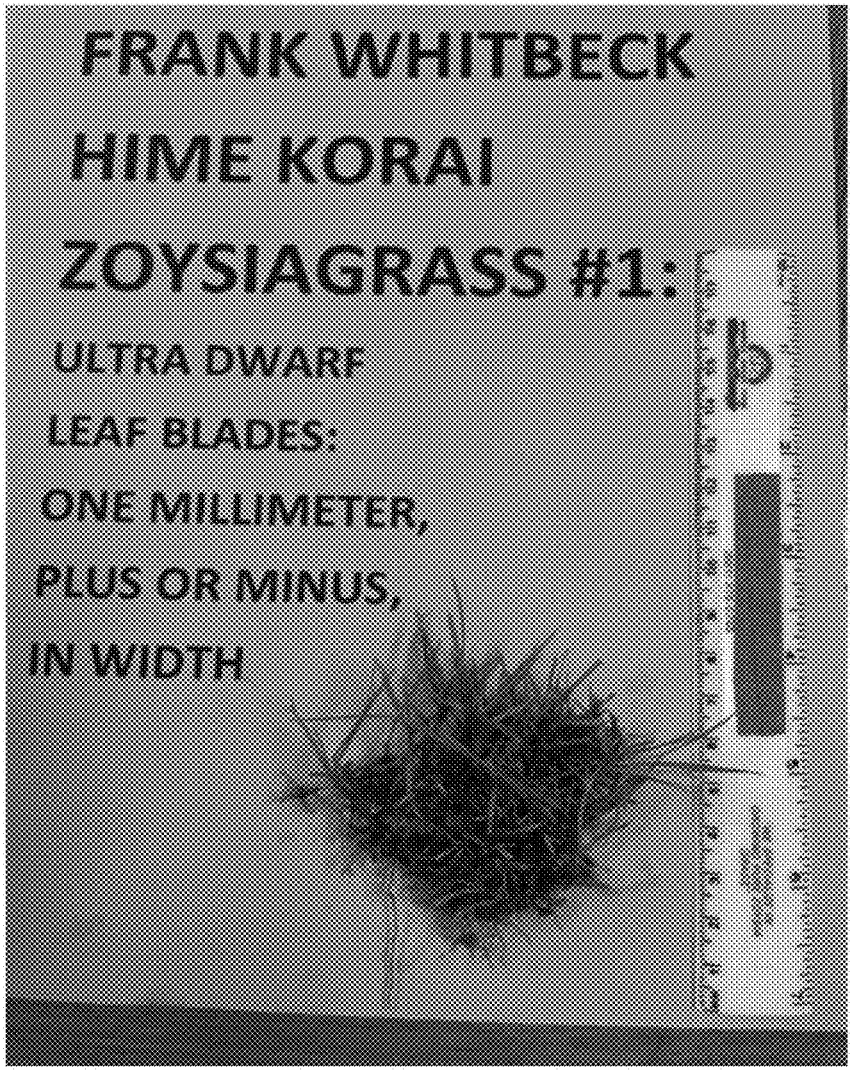
FIG. 3 is a second photograph showing leaves of the claimed new variety.

Leaf Blades:

The new variety is identified by its smooth surfaced ultradwarf leaf blade about 1 millimeter in width in a distinctive Zoysiagrass top growth leaf pattern with at least one leaf blade at a near 90% (right or left) angle in each shoot, as shown in FIGS. 2 and 3. Often there are multiple plants per shoot with multiple near 90% angle leaves. Following establishment, its ultradwarf leaf blade canopy forms such a dense top growth surface that it appears to prevent weed and competing grass competition from taking hold and thriving. The density of its ultradwarf leaf blade canopy, combined with its extremely dense root system, provides a natural barrier to weed and competing grasses, hence drastically reducing at full establishment the necessity of expensive herbicides, fungicides and fertilizers. Leaf blade length depends only on one's preferred mowing height which easily can range from 3 inches in height down to 0.125 inch on a championship golf green. Additionally, the plant appears to withstand scalping in a way that 'Meyer Z-52' Zoysiagrass (a *japonica* Zoysiagrass variety) and other known *matrella* Zoysiagrass varieties cannot handle, particularly in late summer and fall. Leaf scalping in late summer or fall can set back or kill most known Zoysiagrass varieties, but this is less likely with the new inventive plant variety. In addition, the need for turfgrass maintenance, including mowing in late fall, winter, and early spring is reduced to virtually zero as the new variety's plant metabolism slows as it approaches and experiences full or partial dormancy during lower temperatures, especially during December, January, and February. This wintertime reduction in maintenance is extended by slower growth rates in fall (October and November) and early spring (March and April) to approximately half of its prime growing season growth rate (May through September) at any of its preferred mowing heights (see above). Maintenance of shorter mowing heights requires a higher mowing frequency, but only May through September and needing far less mowing than known bentgrass varieties and known hybrid bermudagrass varieties. Normal lawn mowing heights with the plant also require less mowing than most other known turfgrass varieties. Combine that with only an occasional need for herbicides, fungicides and fertilizers primarily in its May through September prime growing season, and the result is a clean, carpet-like lawn surface virtually free of contamination with less maintenance time, effort and expense.

Figure 4:
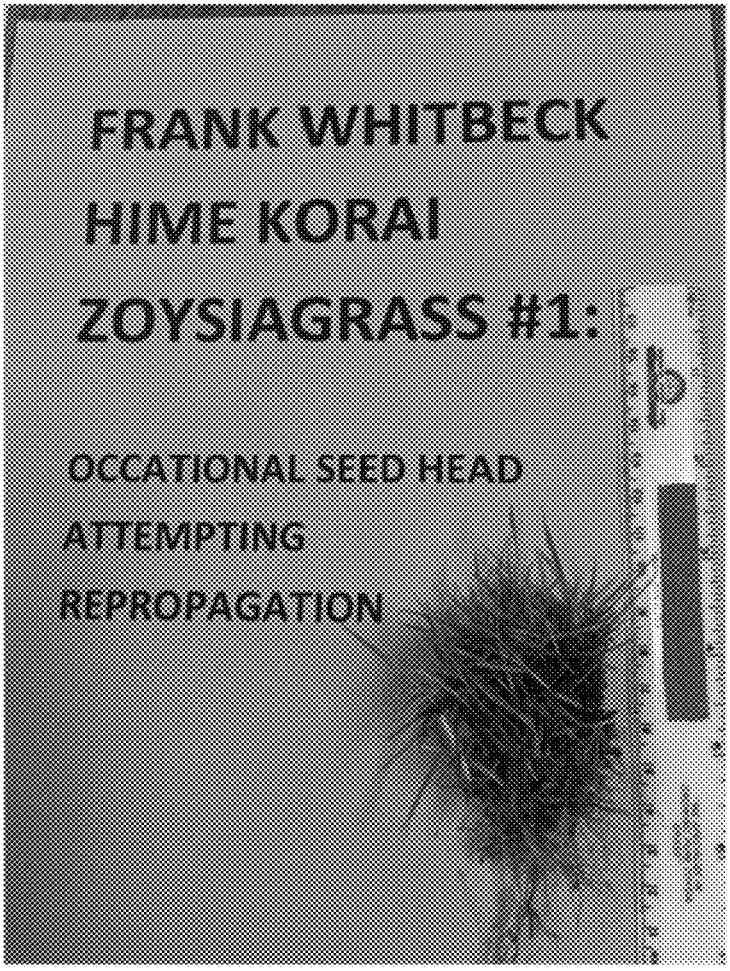
FIG. 4 is a photograph showing seed heads of the claimed new variety.

Seed Heads:

The new plant variety is an aggressive grower for a *matrella* Zoysiagrass with a high tolerance to winter cold. But its occasional seed heads are not aggressive, as shown in FIG. 4. Where there is a highly cultured area like a golf green or where regular mowing is occurring, the plant seed head stays submerged below the leaf canopy as its seed heads (which appear very similar to the naked eye as leaf blades themselves) are regularly clipped off setting back its re-emergence as a seed head until recovery can occur. In higher mowed grass, like a home lawn, the seed head is not readily identifiable either as it is slim like the other one-millimeter width leaf blades and because of its light green color, totally different from the purple *japonica* Zoysiagrass seed head and other *matrella* Zoysiagrass seed heads that also cast a purple hue in the spring.

Extreme Temperature Tolerance:

The claimed new plant variety withstands extreme winter cold temperatures in the transition zone of the United States with a high tolerance for extreme summer heat as well, even at lower golf green mowing heights. An early winter overnight freeze at 0 Celsius (32 degrees Fahrenheit) does not seem to affect the plant as daytime temperatures rise into the 40s, 50s and 60s. There is no freezing of the plant, no change in growth rate, no change in green color, no loss of chlorophyll, and no change in plant health. The inventor has observed a slower growth rate at lower temperatures down to −22.22 Celsius (−8 degrees Fahrenheit) with little change in the plant's green color, as long as daytime temperatures rise back above freezing, the typical pattern of mid-fall to year-end in the transition zone. During the 1990's Dr. John Dunn found that most known *matrella* Zoysiagrass varieties die at around 14° Fahrenheit (−10° Celsius). Dr. Dunn found that Zoysiagrasses named Cavalier, Crowne, Palisades, Emerald and El Toro were killed at 14° Fahrenheit (−10° Celsius) or warmer. Then 'Meyer Z-52' Zoysiagrass was an exception. The new plant variety is also an exception. The new plant variety goes dormant in late December or early January when colder daytime and nighttime temperatures set in around the clock in the transition zone. Winter in the transition zone does not affect the viability or the potential uses of the new plant variety, unlike other warm season turfgrasses. 'Meyer Z-52' Zoysiagrass can withstand −32.2 Celsius (−26 degrees Fahrenheit). The inventor has not yet discovered a naturally occurring low cold temperature that the new plant variety cannot survive, and, is encouraged that −22.2 Celsius (−8 degrees Fahrenheit) is not the lowest temperature that the plant can survive, even at lower golf green mowing heights. Green color retention is very consistent with the plant, right up until January when colder round-the-clock temperatures in the transition zone are relentless. The only observed stress condition with the plant has more to do with being grown in a medium like pure sand without organics, moisture retention, or soil with natural nutrients based in silt and clay. Sand can be easily amended to correct the lack of organics, nutrition, and moisture. Seasonal weather change to below freezing and beyond is the bigger obstacle for most grasses but not with the new plant variety. The claimed new plant variety is an ultradwarf *matrella* Zoysiagrass that has almost the same cold weather tolerances as Meyer, a *japonica* Zoysiagrass. As with Meyer, the new variety's only need when extreme cold or heat occurs is adequate irrigation. The recovery rate of the new plant is faster than that of 'Meyer Z-52' Zoysiagrass, making the new plant "superior," the term used by the USDA in 1955 when 'Meyer Z-52' Zoysiagrass was released by the USDA.

Figure 5:
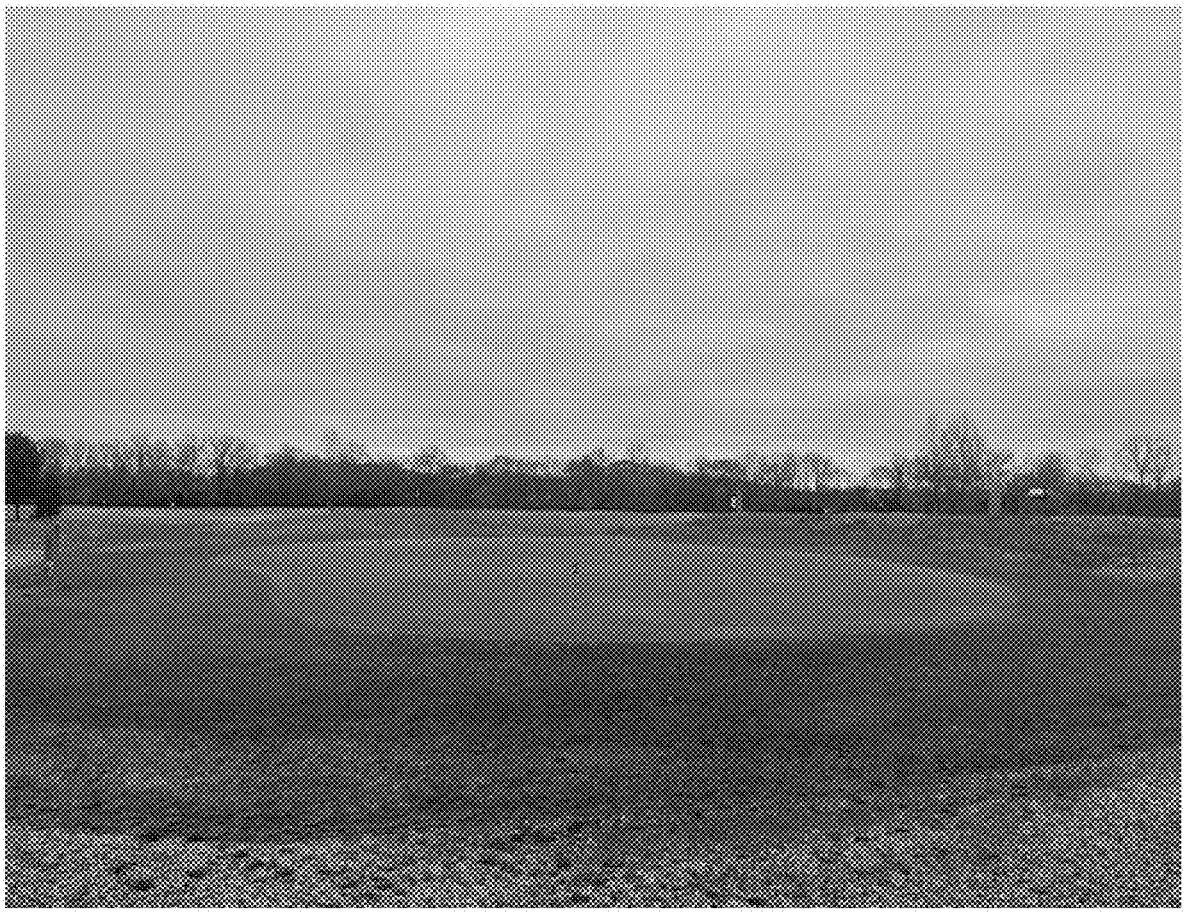
FIG. 5 is a photograph of a golf green planted with the claimed new variety immediately following severe winter cold temperatures. Note the golf green is surrounded by cool season grass and Bermudagrass fairways in full dormancy are in the background.
Figure 6:
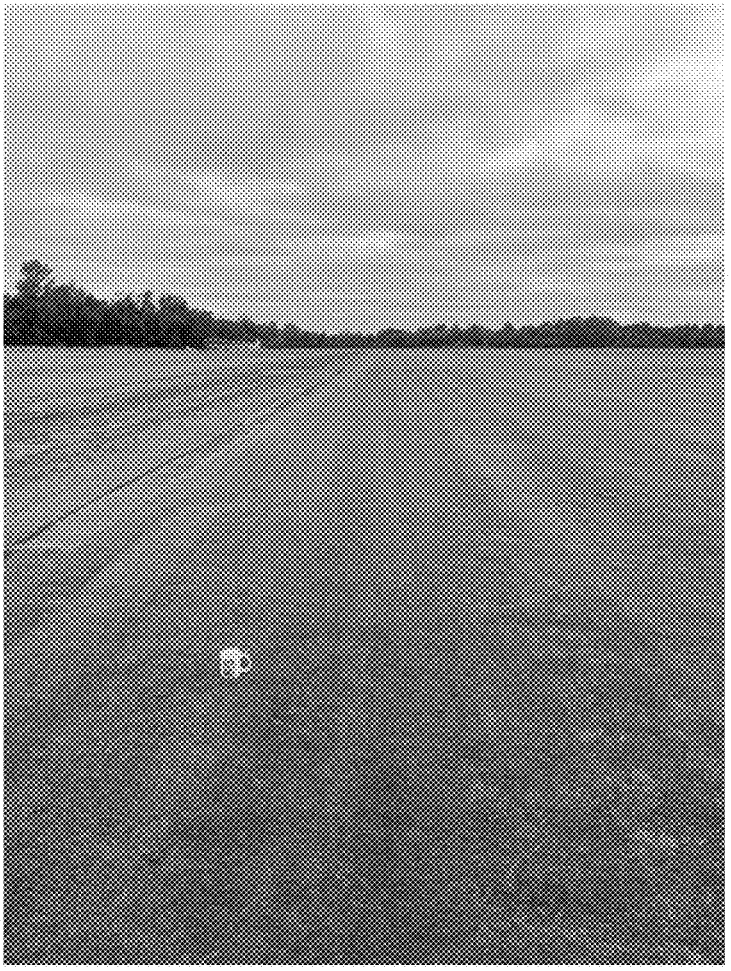
FIG. 6 is a photograph of a nursery plot at a grass farm planted with the claimed new variety.
Figure 7:
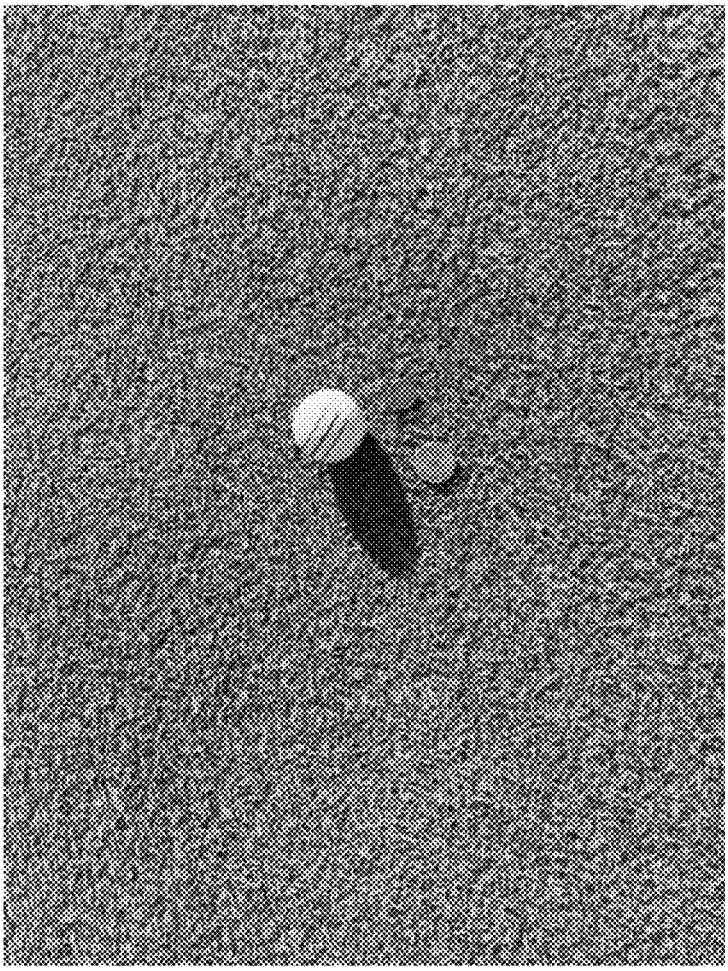
FIG. 7 is a close-up photograph of a golf green planted with the claimed new variety.

FIG. 5 is a photograph of the new plant variety on a golf green in Nashville, Tennessee, the photo being taken on Mar. 13, 2023, following two sub-zero Fahrenheit weather events (−17.778 Celsius) during the previous three months. This golf green has been in play for approximately three years and has never been tarped or taken out of play. FIG. 6 shows a nursery stock of the claimed new variety reel mowed at 500/1000 (½ inch) near Little Rock, Arkansas. This field has never been tarped and no observations of winterkill have been recorded. FIG. 7 shows the new plant variety reel mowed at 170/1000 of an inch on a golf green in Nashville, Tennessee. This push-up golf green was constructed in 2020, was opened for play in the spring of 2021, and has never been tarped or taken out of play.

Four Season Green Color Retention:

The new plant variety has a stability and consistency not found in most turfgrasses. Historically, there have been grasses grown and maintained for the purpose of providing year-round use in virtually every country, with consumers being let down by a particular grass's inability to withstand change in seasonal weather. Cool-season grass seed gets bagged and sold in nurseries nationwide. Yet when they get used in the US transition zone, they die in hot summers. In the transition zone, cool season grasses are temporary grasses. Likewise Bermudagrasses die in the transition zone due to cold weather conditions in winter. Bentgrasses and Bermudagrasses are temporary grasses in the transition zone. Their life can be extended by various chemical applications creating a huge management expense to keep them alive. Consumers, however, seek turfgrasses for all four seasons. In 1955, 'Meyer Z-52' Zoysiagrass was introduced by the USDA as a "miracle grass" that survives all four seasons. There have been very few turfgrasses that have been introduced since 1955 that could claim viability in all four seasons. The claimed new plant variety not only survives in all four seasons, it has a longer green season as a sports turf and as a lawn grass than 'Meyer Z-52' Zoysiagrass, as set forth in the tables below for two different mowing heights:

Normal lawn mowing heights:

| | Meyer Z-52 | New plant variety |
|---|---|---|
| Green color begins | Late March | Early March |
| Green color ends | Mid-November | Late December |

Lower mowing heights on golf greens:

| | New plant variety |
|---|---|
| Green color begins | Late February |
| Green color ends | Early January |

At lower mowing heights (e.g., for a golf green) in the transition zone, the new plant variety has a dormancy period of about two months. 'Meyer Z-52' Zoysiagrass and many other known *matrella* Zoysiagrasses cannot be mowed to a golf green mowing height (only down to ½" before scalping occurs). The new plant variety reduces dormancy by around one-half (from 4 months to 2 months) at lower mowing heights compared to Meyer Z-52.

Figure 8:
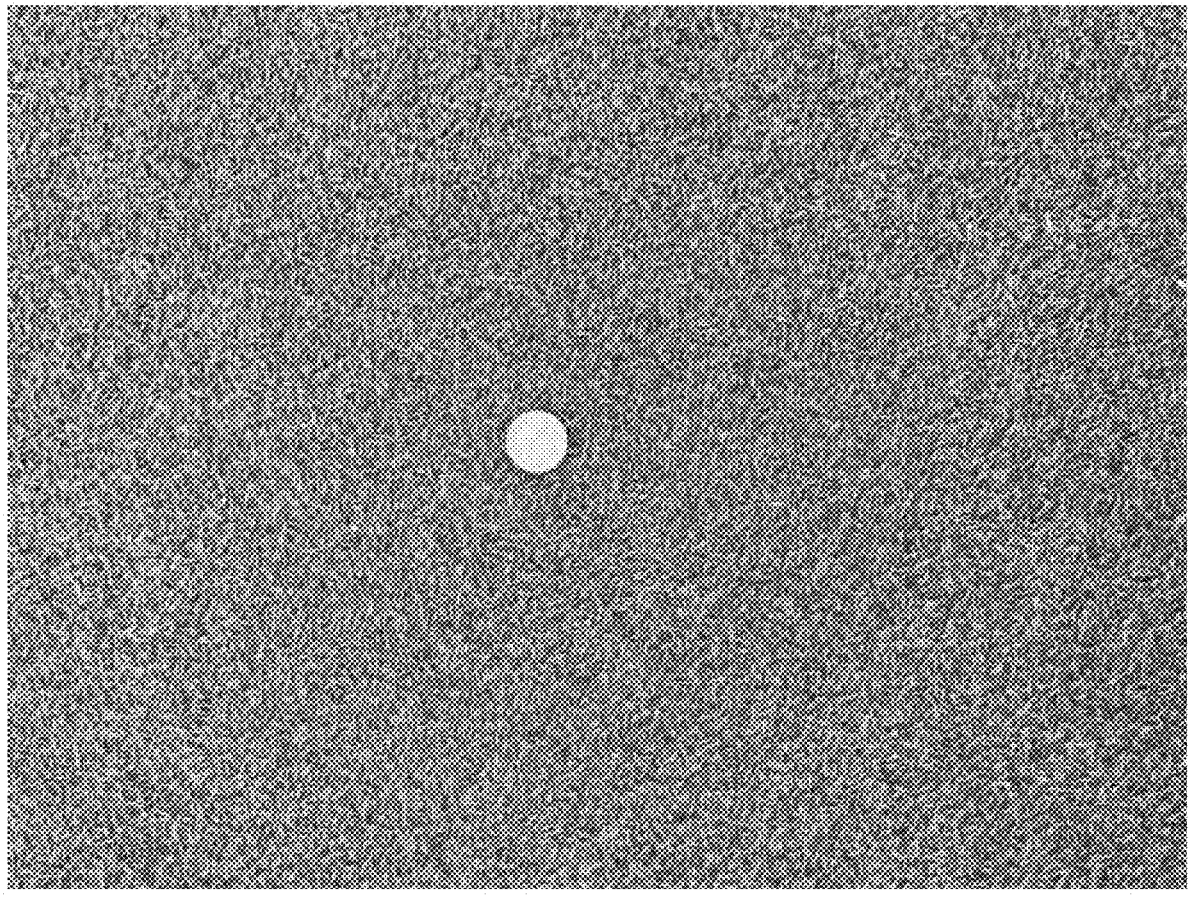
FIG. 8 is a close-up photograph of a golf green during winter season planted with the claimed new variety.

FIG. 8 shows a golf green in Nashville, Tennessee planted with the new plant variety, the photograph taken on Jan. 25, 2024. The figure shows that the new plant variety has suffered only a slight loss of green color in spite of numerous days of frost and below freezing nighttime temperatures as low as zero degrees Fahrenheit and with heavy dormancy appearing in other grasses on the golf course.

Figure 9:
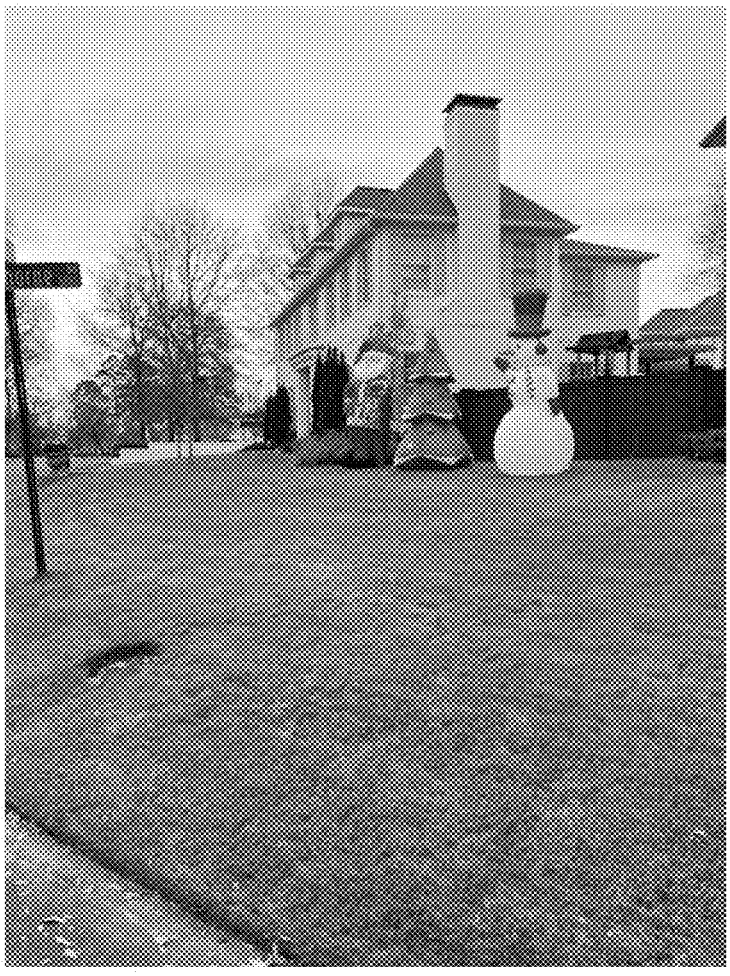
FIG. 9 is a photograph of a first lawn planted with the claimed new variety, the photo being taken around Christmastime in Little Rock, Arkansas.
Figure 10:
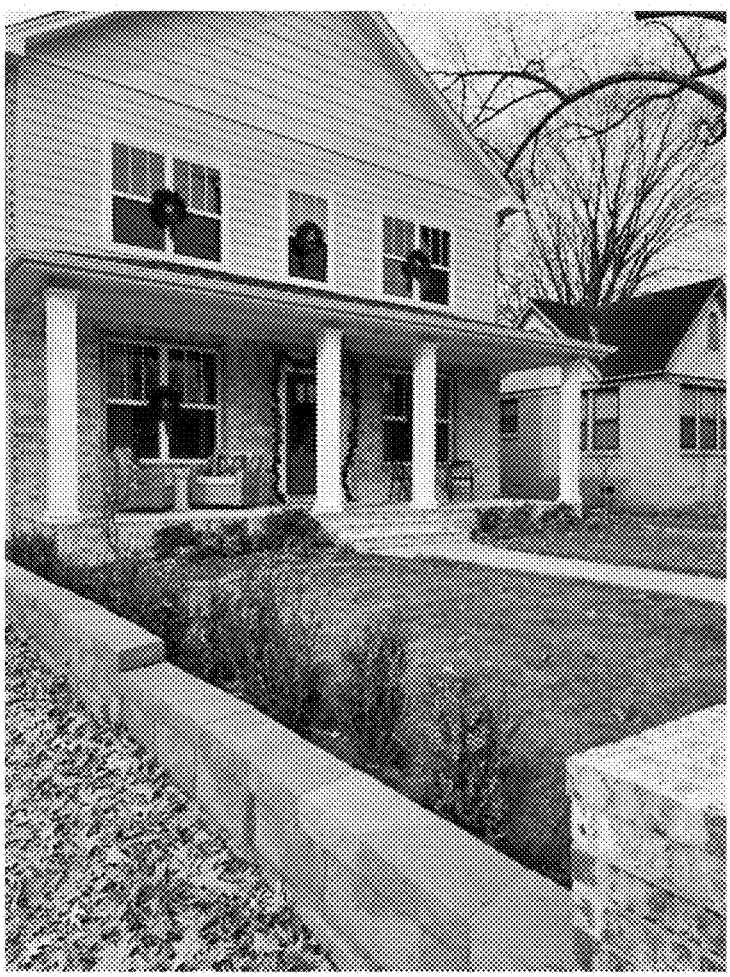
FIG. 10 is a photograph of a second lawn planted with the claimed new variety, the photo being taken around Christmastime in Little Rock, Arkansas.

FIG. 9 shows the new plant variety planted at a home lawn in Little Rock, Arkansas, with the photo taken on Dec. 21, 2023. The figure illustrates that the new plant variety exhibits exceptional green color at Christmastime in Little Rock, Arkansas, while other home lawns are in full dormancy. FIG. 10 shows another home lawn in Little Rock, Arkansas, this photograph also being taken on Dec. 21, 2023, while other home lawns are in full dormancy. It may be noted that the trees in the photograph have completely shed their leaves, the leaves on the ground to the left in the next yard, and the Christmas wreaths on the featured home showing that it is Christmastime.

Year-Round Plant Health:

The new plant variety defies the typical *matrella* Zoysiagrass family problem of not performing well in wintertime or springtime (the same problem most warm season grasses have in the transition zone). Usually lots of chemical amendments (e.g., fungicides) need to be used on *japonica* and *matrella* Zoysiagrass varieties as they do not handle cold weather very well and need some help with plant diseases come spring. Fungicides are a big cure for their ills but these fungicides may be too expensive for most golf courses and homeowners to afford. With the new plant variety, very few diseases caused by winter cold occur and hence there is very little need for fungicides and other herbicides. The new variety has a natural immunity to fungus and plant diseases. Over fertility is usually to blame when such diseases occur in the plant. Over or under watering is another culprit. Usually the claimed new variety plant, when planted in the transition zone, needs no irrigation from Thanksgiving until Easter. But from Easter to Thanksgiving irrigation is necessary, particularly during hot summer weather and during a dry fall season. As with all turfgrasses, the new grass variety needs to be well drained to avoid over-watering. High nitrogen fertilizers also need to be avoided with any Zoysiagrass, and the new plant variety is no exception, as they can weaken any Zoysiagrass variety and reduce its natural resistance to plant diseases.

Shade Tolerance:

The new plant variety is usually grown on farmland or golf courses that are open to full sun and refreshing breezes. However, this new variety has a high tolerance for lower light conditions like partial shade or even full shade where pleasant breezes do not exist. One needs to be vigilant about observing the actual microenvironment the plant has to grow in, for example the quality of the soil, the lack of air flow, the irrigation system, and weekly maintenance. Shade by itself is not a big problem as long as the other ingredients to the lawn are good. Many shade situations need extra water and fertility as the plants that are producing the shade need to be fed. Air flow is important and lower tree limbs should be trimmed. The new plant variety has been grown successfully in north facing lawns with large oak trees where the lawn never sees direct sunlight.

Plant Stability:

The new plant variety is a very stable turfgrass unless something is done to weaken it. Usually leaving it alone to adjust to its environment is the best cure for a problem. Lots of turfgrass problems are manmade, such as hot nitrogen or slow-release fertilizers. Use of an immediate-release, low-nitrogen fertilizer, preferably balanced with potassium and phosphorus, is recommended. There is no need to worry about weed control following establishment with the new plant variety, because it will outgrow and control weeds on its own.

Low Need for Fertilizers and Chemicals:

The new plant variety needs fewer amendments (chemicals and fertilizers) to thrive than virtually every other turfgrass, even other Zoysiagrass varieties. The inventor has for many years grown and sold 'Meyer Z-52' Zoysiagrass throughout the south and southwest, but with the new plant variety one gets closer to a "maintenance fee" lawn or golf course with less of a costly carbon footprint, more landscape architectural beauty, and four-season green color allowing oxygen production and climate cooling from a healthy, natural low-maintenance turfgrass.

Figure 11:
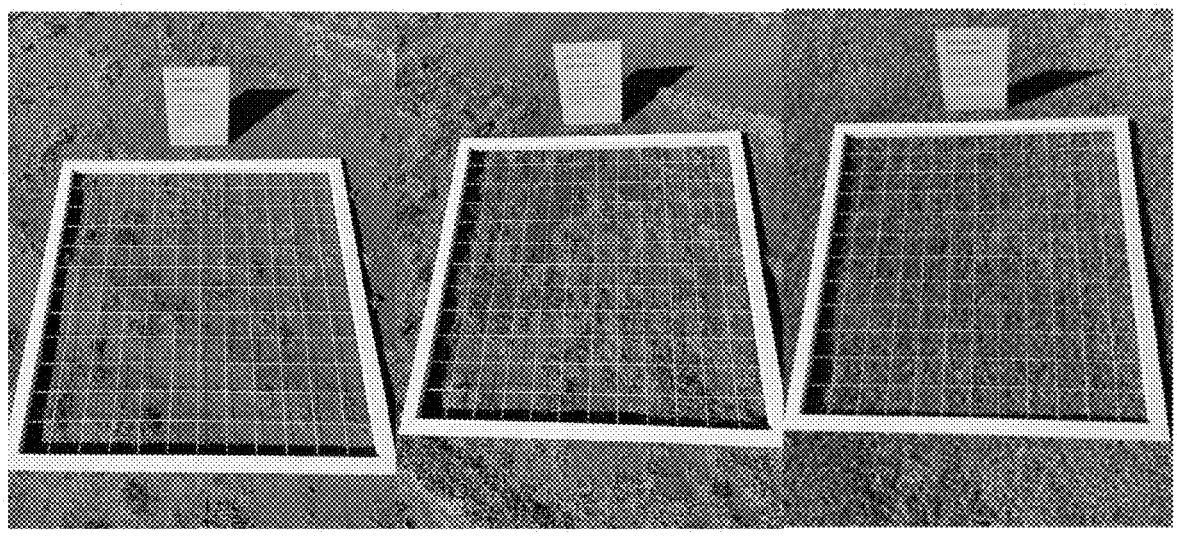
Fig. 11 PRIOR ART
FIG. 11 is a time-series of three photographs showing regrowth after sod harvest for prior art 'Meyers Z-52' Zoysiagrass.
Figure 12:
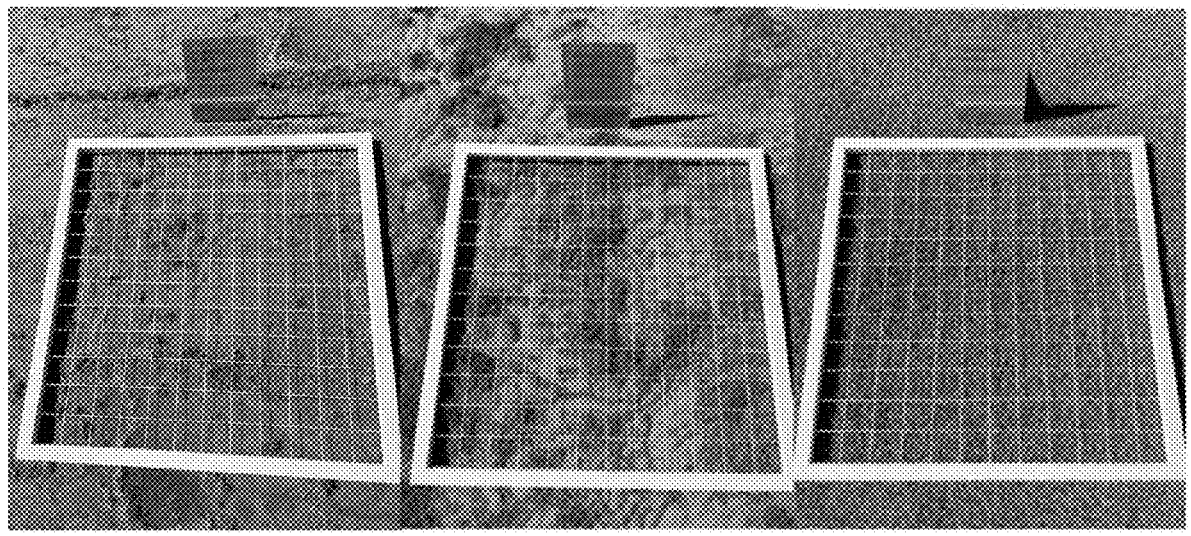
FIG. 12 is a time-series of three photographs showing regrowth after sod harvest for prior art *matrella* Zoysiagrass '#13521.'
Figure 13:
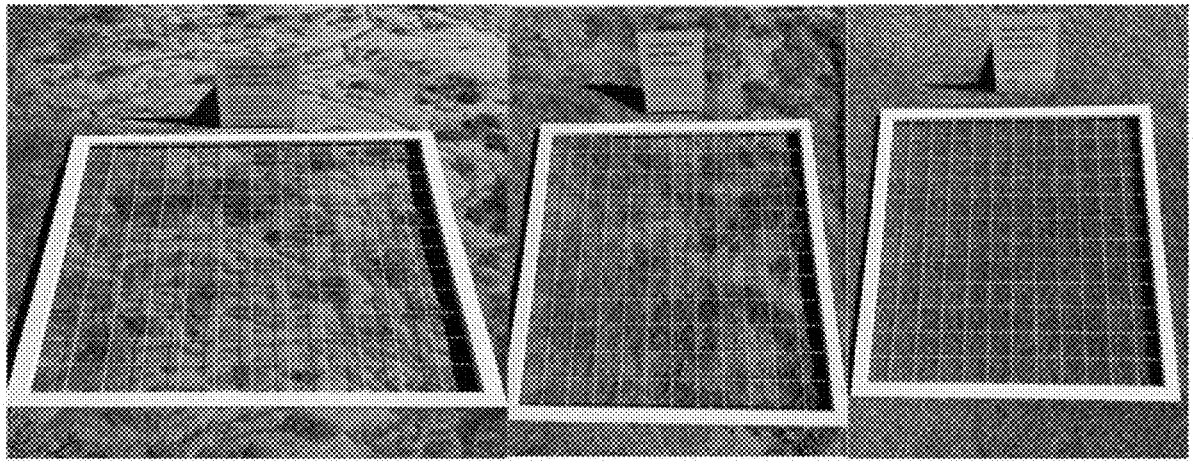
FIG. 13 is a time-series of three photographs showing regrowth after sod harvest for the claimed new variety.

Recovery from Divot Injury, Sod Harvesting, and Foot Traffic:

The growth rate and recovery rate of the new plant variety is higher than that of most other Zoysiagrasses. Many Zoysiagrasses have been marketed with a slower growth rate in mind, because that leads to less mowing. Many uses of Zoysiagrass need faster regrowth to fill in divots or foot traffic injury. FIGS. 11, 12, and 13 are photograph reviews of the growth rate of 'Meyer Z-52' Zoysiagrass, a prior art *matrella* Zoysiagrass '#13521,' and the novel plant variety claimed herein. In each case, the three-month recovery following a sod harvest is shown on the left of the figure, the six-month recovery is shown in the middle of the figure, and the full recovery is shown on the right of the figure. In the case of Meyer Z-52 (FIG. 11), the three-month recovery is approximately 15% after three months, 30% after six months, and almost two full growing seasons are required to reach full recovery. In the case of the prior art *matrella* Zoysiagrass '#13521' (FIG. 12), the three-month recovery is approximately 10% after three months, 25% after six months, and almost two full growing seasons are required to reach full recovery. The growth rate or coverage rate of the new plant variety is significantly faster than the others. As shown in FIG. 12, the three-month recovery after sod harvest for the new plant variety is approximately 20%, the six-month recovery is approximately 45%, and full recovery requires slightly more than one full growing season.

BOTANICAL DESCRIPTION OF THE NEW VARIETY

Origin: In the fall of 1997, the inventor personally selected the original specimen of the *matrella* Zoysiagrass claimed herein from a cultivated area at a golf course nursery located near Jensekikogen in Prefecture Hiroshima, Japan, as it piqued his interest due to certain unique properties not exhibited by other Zoysiagrass plants based on his knowledge of other Zoysiagrass plants. The cultivated area where the original specimen was selected was not contaminated with other Zoysiagrass plants. The inventor immediately sent the new claimed variety specimen to the plant quarantine section of the USDA in Beltsville, Maryland, the variety labeled at the time "Hime Korai." Following one year in quarantine, the inventor received a small plot of the new claimed variety from the USDA quarantine section. The inventor then asexually reproduced the new claimed variety on the irrigated pure fertile ground at his farm near Little Rock, Arkansas by removing bareroot stolons and rhizomes of the new claimed variety from the pot and planting them just under the soil surface on six-inch centers. The initial grow-in from planted sprigs of the new claimed variety to fully maturity establishment took almost two full growing seasons. Noxious cool season and warm season weeds were removed chemically during the grow-in process. Subsequently the inventor took bareroot stolons and rhizomes from the then-mature small plot of the new claimed variety and planted them just beneath the soil surface on a slightly larger plot of irrigated pure fertile ground at his farm near Little Rock, Arkansas. This second asexual grow-in also took approximately two full growing seasons to grow together to a full maturity establishment. This planting process was replicated every two years until the inventor had a one-acre nursery plot with which to study and observe the characteristics of the new claimed variety. No other Zoysiagrass plants, noxious weeds or other weed grasses were allowed to contaminate this new nursery stock area planted with the new claimed variety. Once there was enough plant material of the new claimed variety, plug planting on six-inch centers was adapted for a continuation of the asexual grow-in of a pure nursery stock of the new claimed variety on larger acreage at the inventor's farm near Little Rock, Arkansas.

Parent plant: The parent plant of the claimed new variety is unknown.

Genus: Zoysiagrass.

Classification: *Zoysia matrella*, (L.) Merr.

Variety denomination: "Frank Whitbeck Hime Korai" Zoysiagrass.

Growth habit: The new plant variety is a perennial warm season plant that reproduces asexually by stolons and rhizomes and produces a dense, fine-textured ultra-dwarf turfgrass capable of being mowed to and managed at championship golf green mowing heights.

Leaf blade: Rolled in the bud; flat, smooth surface with leaf blade width of approximately 1 mm and capable of mowing heights from 0.125 inch to 3 inches.

Leaf blade veins: Both adaxial and abaxial leaf surfaces are flat and smooth without hairs and without visible veins unless magnified.

Leaf blade flexibility: Medium softness at lawn-mowing heights while leaf blade stiffness and density increases with lower mowing heights.

Leaf blade length: 0.125 in. (3.175 mm) to 3 in. (76.2 mm); lower mowing height leaf density can be enhanced with verticutting.

Seed heads: The seed heads of the new claimed variety are dwarfed and remain below the leaf blade mowing heights. Seed head production is not prolific in the new claimed variety. Seed head production is not aggressive at any time of the year. It is yet to be determined if the seed of this plant is viable to reproduce the new plant variety.

Royal Horticultural Society (R.H.S.) Plant Color Chart Determination of Leaf blade color: The new claimed variety leaf blade color, both adaxial and abaxial, is RHS #131 B.

RHS Plant Color Chart Determination of Root stem color: The new claimed variety stolon and rhizome stem color is RHS #150 D.

Unique characteristics differentiating the new claimed variety from other Zoysiagrass varieties: 1. Extremely dense root system of stolons and rhizomes approximately 1 mm in width and with average length of one foot that is so dense so as to naturally choke out and prevent weed contamination or weed grass contamination. 2. Extremely dense ultra-dwarf leaf blade top growth with leaves of approximately 1 mm in width so as to naturally choke out weeds and weed grasses and naturally prevent contamination. 3. Four-season green color retention with winter dormancy mostly limited to January and February in the "transition zone" of the United States. 4. Survives extremely cold weather including −8° Fahrenheit (−22.22° Celsius) as well as survives extreme summer hot weather well above 100° Fahrenheit. The new claimed variety has never been tarped for winter protection even at golf green mowing heights. 5. Extremely stable plant needing virtually no chemical herbicides, fungicides or pesticides following full establishment. 6. Needs very little nitrogen fertilizer to thrive. A blended fertilizer like 13-13-13 is recommended during warm months (May through September). 7. Seed heads are dwarfed and remain below the mowing height in all seasons at all mowing heights. 8. Recovers from injury faster than other known Zoysiagrass varieties including foot traffic, divots and sod harvesting. 9. Highly shade tolerant and is known for producing a thick and dense stands of grass even if planted under large oak and maple trees and in north-facing lawns. 10. Mowing heights as low as 0.125 inch (⅛ inch) on championship golf greens with no tarps needed for protection from winter cold.

REFERENCES

Dunn, John H., "Low Temperature Tolerance of Zoysiagrasses," February 1999, HortScience Vol. 34 (1).

Dunn, John H., "Zoysiagrass on the Fast Track," Golf Course Management, June 1999.

Dunn, John H., "The Cutting Edge," Golf Course Management, June 1998.

Dunn, John H., "Go Easy on Nitrogen for Zoysiagrass Root Growth," Golf Course Management, April 1998.

Samples, Tom, "ZoysiaGrasses: An Update (with John Sorochan)," Tennessee Turfgrass, October/November 2018.

I claim:

1. A new and distinct variety of *matrella* Zoysiagrass named "Frank Whitbeck Hime Korai", as herein illustrated and described.

* * * * *

(note millimeter scale on left side of ruler)

(note millimeter scale on left side of ruler)

(note millimeter scale on left side of ruler)

(note millimeter scale on left side of ruler)

PRIOR ART